United States Patent [19]
Selick et al.

[11] Patent Number: 6,043,027
[45] Date of Patent: Mar. 28, 2000

[54] MULTI-WELL SINGLE-MEMBRANE PERMEATION DEVICE AND METHODS

[75] Inventors: Harold E. Selick, Belmont; Gregory A. Smith, Union City; John W. Tolan, San Carlos, all of Calif.

[73] Assignee: Glaxo Wellcome Inc., Research Triangle Park, N.C.

[21] Appl. No.: 09/178,723

[22] Filed: Oct. 26, 1998

Related U.S. Application Data

[63] Continuation-in-part of application No. 08/959,434, Oct. 28, 1997, Pat. No. 5,962,250.

[51] Int. Cl.$^7$ ...................................................... C12Q 1/00
[52] U.S. Cl. .................. 435/4; 435/288.4; 435/288.5; 435/297.5; 422/101; 436/178; 436/809
[58] Field of Search ........................... 422/101; 435/288.4, 435/288.5, 297.5, 4; 436/178, 809

[56] References Cited

U.S. PATENT DOCUMENTS

| | | |
|---|---|---|
| 4,871,674 | 10/1989 | Matsui et al. . |
| 4,894,343 | 1/1990 | Tanaka et al. . |
| 4,948,442 | 8/1990 | Manns . |
| 5,026,649 | 6/1991 | Lyman et al. . |
| 5,028,541 | 7/1991 | Kiel et al. . |
| 5,047,215 | 9/1991 | Manns . |
| 5,068,195 | 11/1991 | Howell et al. . |
| 5,089,385 | 2/1992 | Kiel et al. . |
| 5,139,946 | 8/1992 | Howell et al. . |
| 5,183,744 | 2/1993 | Kawamura et al. . |
| 5,183,760 | 2/1993 | Sweetana et al. . |
| 5,272,081 | 12/1993 | Weinreb et al. . |
| 5,273,718 | 12/1993 | Sköld et al. . |
| 5,409,829 | 4/1995 | Mussi et al. . |
| 5,468,638 | 11/1995 | Barker et al. . |
| 5,490,415 | 2/1996 | Mak et al. . |
| 5,506,141 | 4/1996 | Weinreb et al. . |
| 5,510,262 | 4/1996 | Stephanopoulos et al. . |
| 5,591,636 | 1/1997 | Grass . |
| 5,599,688 | 2/1997 | Grass . |

FOREIGN PATENT DOCUMENTS

| | | |
|---|---|---|
| 1 509 826 | 5/1978 | United Kingdom . |
| WO 94/06902 | 3/1994 | WIPO ............................... C12M 3/06 |
| WO 97/06890 | 2/1997 | WIPO ............................... B01L 3/00 |

*Primary Examiner*—David A. Redding
*Attorney, Agent, or Firm*—Darin J. Gibby; Lauren L. Stevens

[57] ABSTRACT

The invention provides exemplary testing devices, systems, and methods for evaluating the permeation of various chemicals through different types of cells. In one exemplary embodiment, a testing device is provided which comprises a base member and a top member having a plurality of wells which are aligned when the top member is secured to the base member. A membrane sheet which includes at least one layer of cells grown on the sheet is placed between the base member and the top member prior to assembly. Test samples are placed into the wells in the top member and samples are removed from the top and bottom wells at a later time and tested to determine the amount of test sample which permeated through the cells.

33 Claims, 3 Drawing Sheets

MULTI-WELL SINGLE-MEMBRANE PERMEATION DEVICE AND METHODS

CROSS REFERENCE TO RELATED APPLICATIONS

This application is a continuation in part application of U.S. patent application Ser. No. 08/959,434, filed Oct. 28, 1997, now U.S. Pat. No. 5,962,250 the complete disclosure of which is herein incorporated by reference.

BACKGROUND OF THE INVENTION

This invention relates generally to the field of testing systems and methods, and more particularly to systems and methods for transport or permeation testing. In one particular aspect, the invention provides systems and methods for culturing cells onto a membrane and then using the membrane to simulate an epithelial cell layer, such as the cells which form the inner lining of a human intestine, the blood-brain barrier or blood vessels. In this way, transport or permeation tests may be performed using the membrane.

In humans, ingested food passes from the stomach to the small intestine where proteins, fats, carbohydrates and other nutrients are absorbed and distributed into circulation for use in various organs and cells throughout the body. The small intestine is about five to six meters in length and has an extremely large surface area for absorbing nutrients and other materials. The interior of the small intestine includes the mucosal epithelium which comprises small fingerlike projections called villi which protrude into the intestinal lumen and provide the nutrient absorption surface.

For a variety of reasons, it is desirable to study and evaluate how various drugs and other chemicals which are orally ingested by a human will be absorbed into the blood stream through the intestinal wall. Such evaluation can be useful in, for example, drug testing to determine how various drugs would permeate through the intestinal wall and be absorbed into the blood stream after being orally ingested. Determining transport of various substances through other types of epithelial cells can also be useful in therapeutically treating patients.

In order to evaluate how certain chemicals or other substances will permeate epithelial cells, some have proposed growing mammalian-based cells on a membrane which in turn is used to mimic a cell layer within the body. Some previously proposed testing systems comprise a cup having a membrane at its bottom end. After the cells have grown onto the membrane, the cup is inserted into a larger cup or well and various chemicals are placed into the upper cup to evaluate how the chemicals will permeate the cells on the membrane and enter into fluid in the bottom well.

Such testing systems suffer from a variety of drawbacks, including the significant amount of time required to separately seed the cells into each of the upper cups and to add and replace cell culture nutrients in each cup at regular intervals. A further drawback to such systems is their limited use in accommodating smaller sized membranes. For example, many multi-well plates are being provided with increased numbers of wells whose dimensions are significantly smaller to create larger densities of wells within the plates. Accordingly, each upper cup and its membrane needs to be made smaller in order to fit within the smaller wells. However, when reducing the size of the membranes with the testing systems described above, the membrane's surface area may be too small to provide an adequate transport interface. In turn, this can lower concentrations or transported amounts to levels which restrict analytical methodologies presently available to quantify results. Further, the activity provided by a cell layer on such small membrane sizes may not be representative of the activity provided by a cell layer on a larger membrane.

Hence, for these and other reasons, it would be desirable to provide systems and methods which will allow cells to be seeded and cultured in an efficient manner. Further, it would be desirable to provide a design for a testing system where membrane densities are greatly increased while still being sufficiently sized to effectively accommodate cell growth and to provide an adequate transport interface.

SUMMARY OF THE INVENTION

The invention provides systems, devices and methods that are useful in performing various transport or permeation tests, preferably in order to simulate the transport of various substances through epithelial cell layers, such as the cells which line the human intestine, the blood-brain barrier, blood vessels, and the like.

In one exemplary embodiment, the invention provides a testing device which comprises a base member having a plurality of wells. A top member is also provided having a plurality of apertures which correspond to the wells of the base member. A membrane sheet is further provided to receive a layer of cells and to be placed between the top member and the base member, forming top and bottom wells. In this way, a substance that is placed within the top wells may permeate through the membrane and into the bottom wells. The membrane is removable from the device to allow cells to be grown on the membrane before insertion into the device. Such a system is therefore advantageous in that the cells may be seeded and grown on the membrane in an appropriate environment. The membrane sheet may then be placed between the base member and the top member to facilitate a testing procedure. Such a system is particularly advantageous in that only one membrane sheet is seeded with cells and cultured for each multiple-well device. In this way, testing of substances is made more efficient because multiple wells share the same membrane which is easily placed between the top and base members.

In a further aspect, the wells are arranged in a two-dimensional array of rows and columns. Preferably, the arrangement of these rows and columns is chosen to be compatible with multi-well pipettes or automated liquid handling systems to further facilitate testing procedures. Optionally, a gasket may be provided and be placed between the base member and the membrane or between the top member and the membrane to provide a seal between the membrane and base member or the top member. In another aspect, a securing mechanism may be provided to secure the top member to the base member.

In another aspect, the membrane is constructed from materials such as polytetrafluroethylene, polyethylene, PET, polycarbonate and the like. Further, to facilitate growth of the cells the surface area of the membrane may be framed to constrain growth of the cells onto the membrane and to provide rigidity to the membrane. As one example, the frame may comprise a ring or cup-shaped (or other geometrically shaped) member which is disposed about a periphery of the membrane. In one particular aspect, the cells seeded and cultured on the membrane comprise mammalian-based cells.

In a still further aspect, the base member is constructed with a partial wall whose shape is complementary to the shape of the membrane and its frame. This wall acts as a guide to ensure reliable and reproducible insertion of the membrane into the device without damaging any cells on the membrane. One particular advantage of using a cup-shaped frame is that the top member may be held within the frame, with the frame (in combination with the guide of the base member) serving to align the apertures of the top member with the wells of the base member. In another aspect, one ore more pins protrude from a bottom face of the top member and correspond to holes in a top face of the base member. The pins and corresponding holes assist in the alignment of the apertures in the top member with the wells in the base member, and prevent rotational stress on the layers of cells.

In one particular embodiment, the apertures in the top member have a larger cross-section than the wells of the base member. This may be accomplished, for example, by bevelling a bottom edge of the apertures in the top member. In this way, the top member does not crush the cells near the edge of the wells in the base member when the top member is forced against the base member to make a seal.

In one particular aspect, multiple base members may be provided with different sized wells. In this way, different base members may be employed to control the flow rate of the substance through the membrane.

In another aspect, the system further includes a means for measuring the concentration or other characteristic of a substance within each chamber after the substance has been placed into one of the chambers and has diffused into the other chamber. In this way, the permeation rate of the substance through the membrane and cell layer may be determined. To facilitate evaluation of the characteristic, samples from the lower well may be obtained either by removing the membrane sheet from the base layer or by puncturing the membrane sheet with a sampling device.

In a preferable aspect, the evaluated characteristic is the concentration of the substance. In this way, the permeation rate of the substance through the cells on the membrane may be determined based at least in part on the measured concentrations of the substance within the top and bottom wells after a given period of time. To facilitate evaluation, the substance preferably comprises a chemical which is contained in a buffer which is identical or similar to the buffer in the top and bottom wells.

In one optional aspect, the wells may be filled with a buffer solution prior to placement of the membrane sheet between the top member and the base member. In another aspect, the substance may be maintained within a desired temperature range while permeating the membrane sheet. One particularly advantageous feature of the method is that the membrane sheet may be either horizontally oriented or vertically oriented during permeation.

DETAILED DESCRIPTION OF THE SPECIFIC EMBODIMENTS

Figure 1:
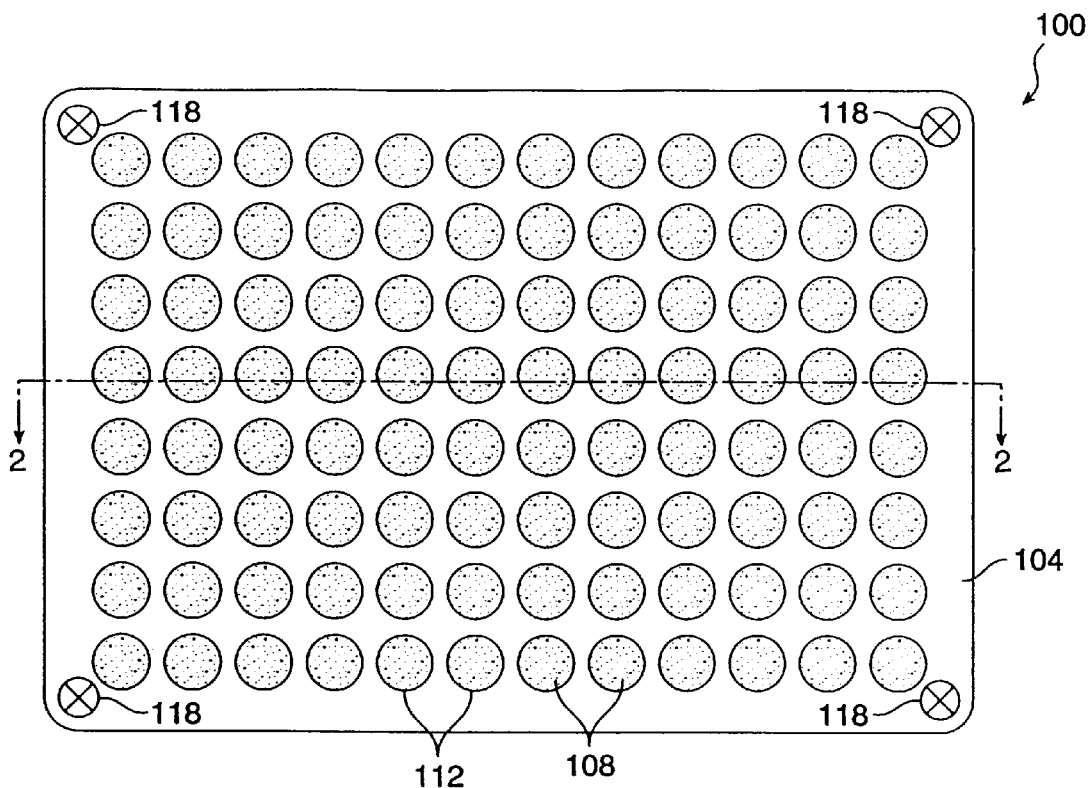
FIG. 1 is a top view of an exemplary testing system according to the invention.

The invention provides systems, devices and methods for testing and evaluating the transport or permeation of various substances through a layer of cells, and particularly epithelial cell layers, including those found in blood vessels throughout the body, the intestine, the blood-brain barrier and the like. Although useful in a wide variety of simulation applications, the invention will find use in modeling intestinal permeation of drug-like compounds.

According to the invention, mammalian-based cells are seeded on a membrane while the membrane is in a generally horizontal orientation. Such an orientation is preferably employed to facilitate attachment of the mammalian-based cells to the membrane. The membrane is then inserted between a base member having a plurality of wells and a top member having a plurality of apertures, with at least some of the apertures corresponding to the wells of the base member. The assembly of the membrane between the base member and the top member forms top and bottom wells.

Once the membrane is inserted, various substances may be introduced into the top wells where they will permeate through the cells on the membrane into the bottom wells. The permeation rate may be determined by measuring the concentration levels or other properties over time in both the top wells and the bottom wells. In this way, a scientist will be able to evaluate the permeation of various substances through the cells in order to model how the human body will absorb such substances through the intestinal wall.

The system of the invention will preferably employ a cell culture device which maintains cells in a tissue culture media until the cells are ready to be seeded onto the membrane. Preferably, the cells will be mammalian-based cells and the membrane will preferably be constructed of a porous material, such as a polytetrafluroethylene (commonly referred to as Teflon), polyethylene, PCT, polycarbonate, or the like. For convenience of handling, the membranes will preferably be surrounded by a raised edge or wall to constrain the growth of the cells to the membrane and to maintain rigidity of the membrane. In this way, growth of the mammalian-based cells onto the membrane will be facilitated.

Either prior to or following insertion of the membranes into the wells, both the top wells and bottom wells will preferably be filled with a buffer solution. A variety of substances may then be introduced into the top wells where they will diffuse through the membranes and into bottom wells. Exemplary substances which may be introduced into the donor chambers include a wide variety of drug compounds, chemicals, and the like.

To facilitate introduction of such substances, the invention will preferably include a fluid delivery device, such as a pipette or a multi-channel pipette. This may be done in an automated or manual manner. Following introduction of the substances into the top wells, various concentration or other measurements will be taken over time in both the top wells and bottom wells to determine the permeation rate of the particular substance through the cells. The particular concentration may be evaluated using commercially available measuring equipment, such as an HPLC, and a mass spectrometer, a fluorescence plate reader, an absorbance spectroscopy plate reader, and the like.

Figure 2:
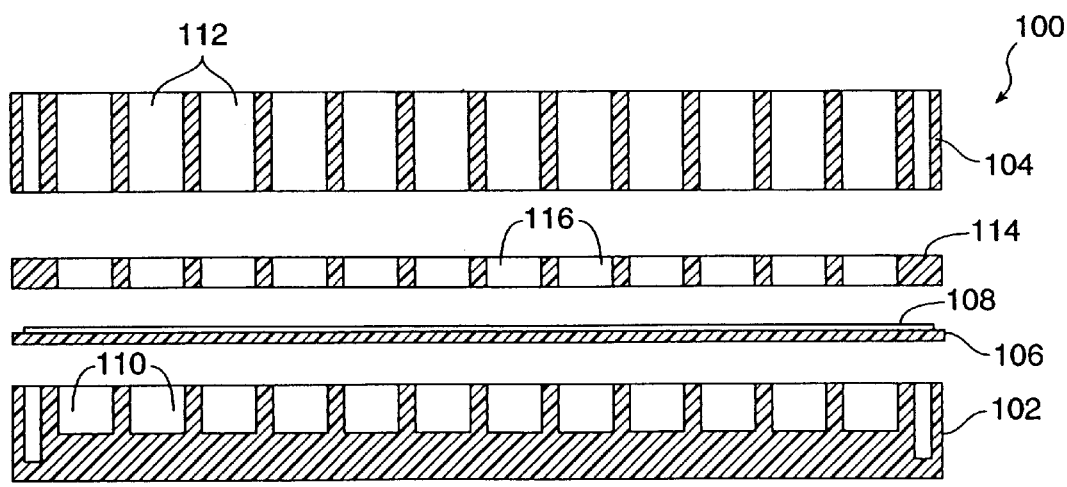
FIG. 2 is an exploded cross-sectional side view of the system of FIG. 1 taken along lines 2—2.

Referring now to FIGS. 1–2, an exemplary embodiment of a testing system 100 for measuring the apparent permeability values of compounds through monolayers of cells that are immobilized on a membrane in a high throughput manner will be described. System 100 comprises a base member 102, a top member 104 and a membrane sheet 106. Membrane sheet 106 includes at least one layer of cells 18 which are preferably grown on membrane sheet 106 prior to being placed between base member 102 and top member 104.

Base member 102 includes a plurality of wells 110 which are aligned with a plurality of apertures 112 within top member 104 when top member 104 is aligned with and secured to base member 102.

Optionally provided is a gasket 114 having a plurality of apertures 116 which correspond to apertures 112 of top member 104 to assist in providing an appropriate seal between top member 104 and the membrane sheet 106 or the base member 102 and the membrane sheet 106 when secured together. A variety of securing mechanisms and devices may be employed to secure top member 104 to base member 102, such as, for example, clamps, screws, and the like. For instance, as illustrated in FIG. 1, a plurality of screws 118 extend through top member 104 to hold top member 104 to base member 102. Top member 104 and based member 102 will preferably include flat surfaces so that an adequate seal will be provided to prevent liquids from leaking from apertures 112 or wells 110.

Membrane sheet 106 will preferably constructed of a porous material, such as polycarbonate, PTFE, and the like. Membrane sheet 106 is removable from the system so as to allow cells to be grown onto the sheet to confluency, preferably as determined by their transepithelial electrical resistance (TEER) or impermeability to appropriate marker compounds (e.g., lucifer yellow).

Base member 102 will preferably include 96 wells which are arranged in a conventional format so that system 100 may be used with standard tools designed for use with 96 well microtiter dishes. For example, by arranging system 100 in this manner it may be readily integrated into a robotocized platform which performs compound addition, sampling, and analysis manipulations. However, it will appreciated that other numbers of wells and format types may be employed within the principles of the present invention.

In use, cells are preferably grown onto membrane sheet 106 as previously described in this application. Wells 110 of base member 102 are then preferably filled with an appropriate transport buffer solution. When system 100 is used in a horizontal orientation, each of wells 110 will preferably be filled to capacity. If used in a vertical orientation, wells 110 may be filled to less than capacity.

Membrane sheet 106 containing cells 108 is then inserted between base member 102 and top member 104 as illustrated in FIG. 2. Members 102 and 104 are then secured together so as to form a junction to prevent liquids from leaking around membrane 106. When appropriately secured together, apertures 112 are filled with a buffer containing an appropriate test compound or compounds.

For testing in the horizontal orientation, system 100 is placed at an appropriate temperature for a desired length of time. Optionally, system 100 may be shaken during the testing procedure. The solution within apertures 112 is then removed and each aperture 112 is washed and aspirated to remove any residual compound. The solutions within cells 110 are then evaluated to determine the concentration of the test compound that has permeated through membrane sheet 106. Access to wells 110 may be accomplished by puncturing membrane sheet 106, e.g., with a pipette, or by disassembling system 100. For testing in the vertical orientation, a cover will preferably be placed over apertures 112 to prevent spillage of their contents. Testing then proceeds as previously described for the horizontal orientation.

Based on the concentration of the substance within wells 110, the apparent permeability of the compounds through cells 108 may be determined. By providing a large number of wells, system 100 facilitates the ability to conduct permeation studies with multiple compounds simultaneously. Further, when the wells are arranged in a standard format, standard tools designed for use with 96 well microtiter plates may be employed. Arrangement of wells 110 is further advantageous in that testing may occur with considerably less compounds than has been required with other approaches. Further, by constructing membrane sheet 106 to be removable, the cell monolayers may be prepared in an efficient manner to further facilitate the testing procedure.

While system 100 has been illustrated in a 96 well format, it will be appreciated that a variety of well shapes, geometries, sizes, and the like may be employed within the principles of the invention. System 100 may optionally contain electrodes for determining TEER (Trans-Epithelial Electrical Resistance) values. Further, sampling portions may be provided to facilitate sample addition and removal. Temperature control capabilities could also be provided to monitor and control the temperature during the testing procedure.

Figure 3A:
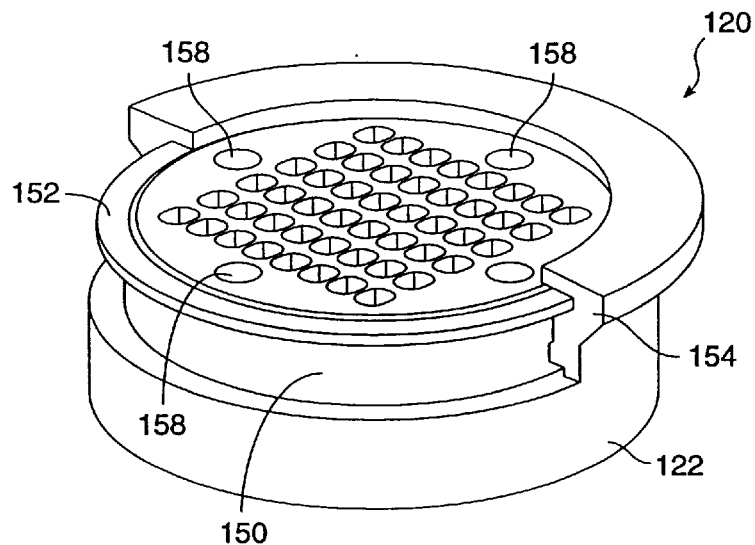
FIG. 3A is a perspective view of another exemplary testing system according to the invention.
Figure 3B:
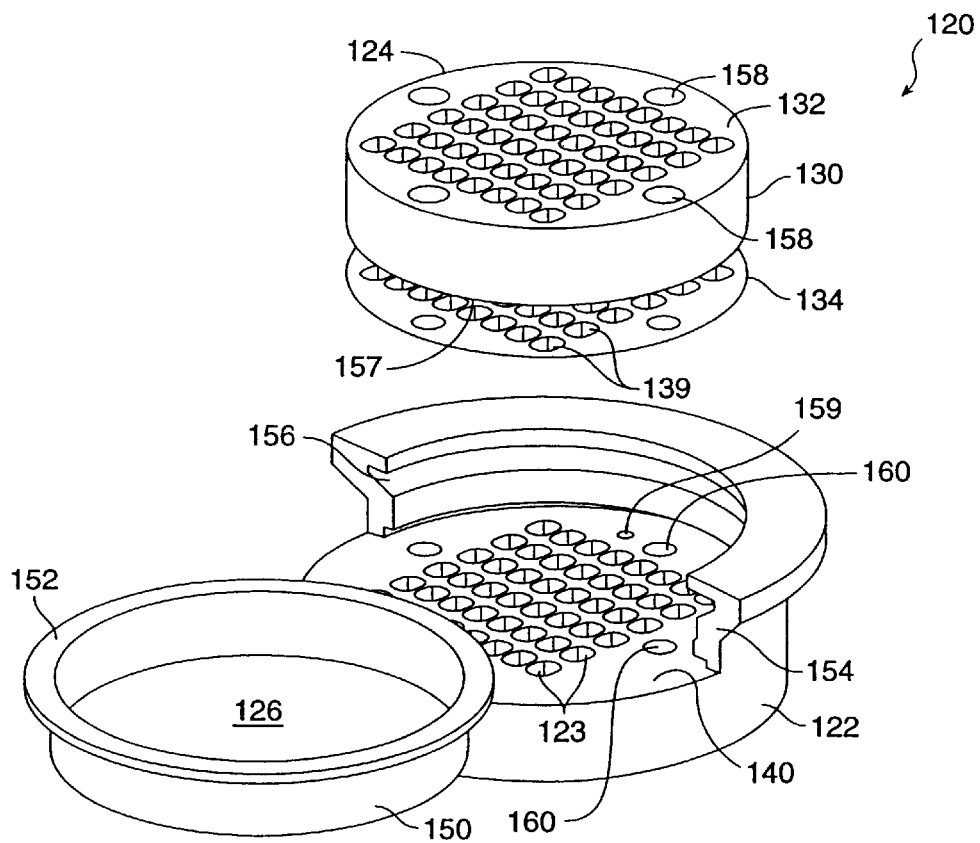
FIG. 3B is an exploded view of the testing system of FIG. 3A.
Figure 4:
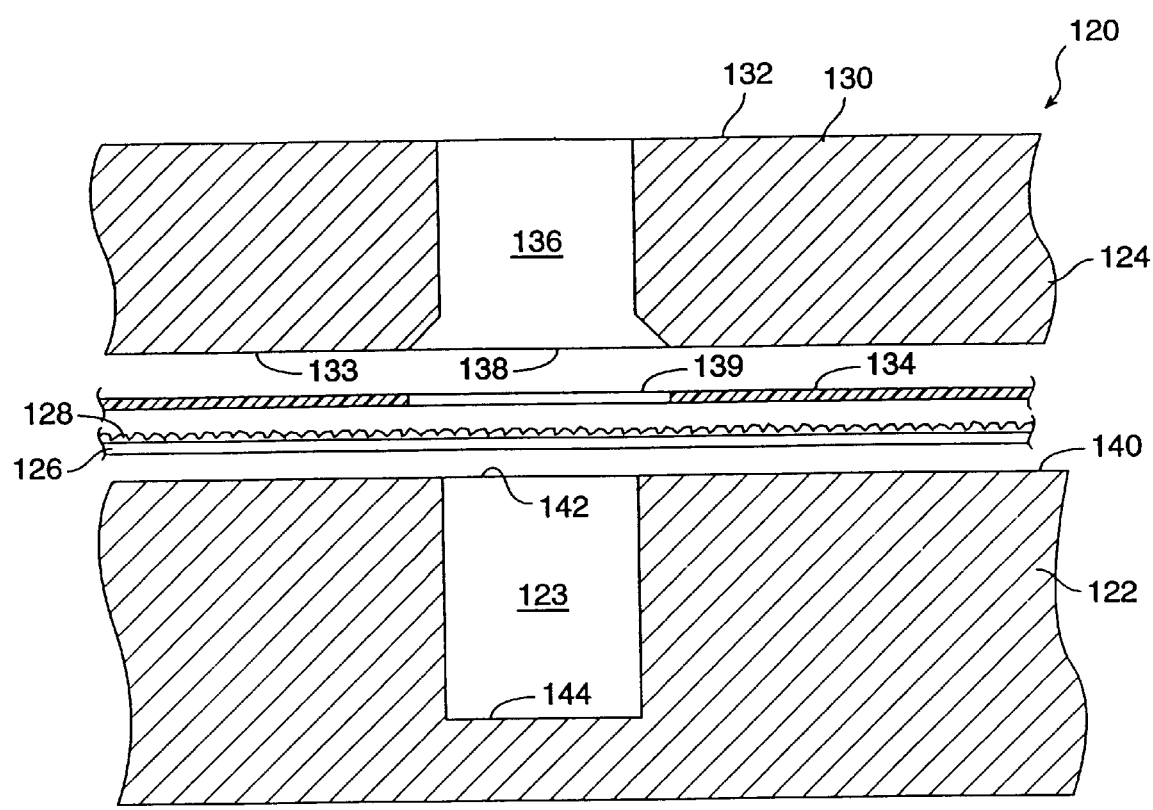
FIG. 4 is an exploded cross-sectional side view of the system of FIG. 3A.

Referring now to FIGS. 3A, 3B and 4, a preferred embodiment of a testing system 120 for measuring the permeability of compounds through cell monolayers will be described. System 120, similar to system 100 described above, comprises a base member 122 having a plurality of wells 123, a top member 124 and a membrane sheet 126. Membrane sheet 126 includes a layer of cells 128 which are preferably grown on membrane sheet 126 prior to its being placed between base member 102 and top member 124.

Top member 124 comprises a cylindrical body 130 having an upper face 132 and a lower face 133, and may optionally be used with a gasket 134. Top member 124 further includes an array of apertures 136 spaced to correspond to and align with wells 123 in the base member. Each aperture extends from upper face 132 to lower face 133 to form a plurality of bottom openings 138 in lower face 133. Each of bottom openings 138 defines an aperture perimeter. Gasket 134 also include openings 139 which preferably correspond in size and shape to openings 138.

Base member 122 includes a top face 140. Wells 123 of base member 122 each have a top end 142 defining a well perimeter in top face 140, and a bottom end 144.

Referring now to FIG. 4, for each corresponding aperture and well, the aperture perimeter (defined by openings 138 in top assembly 124) is greater than the well perimeter (at top ends 142 in base member 122). This may be accomplished, for example, by bevelling the edges of openings 138. This feature results in a more reliable seal between top member 124 and base member 122. Specifically, when layer of cells 128 is contacted with either gasket 134 or lower face 133 of top member 124, cells adjacent the aperture perimeter tend to get damaged, disrupting the integrity of the cell monolayer in that region. If the aperture perimeter is identical to or smaller than the well perimeter, such a disruption in monolayer effectively short-circuits the monolayer system, rendering that well unreliable or ineffective at measuring permeability across the monolayer.

According to the present invention, however, effects of disruptions of the cell monolayer by an overlying top member 124 are minimized by isolating such disruptions to regions outside the well perimeter. This, in combination with the natural seal that forms between the bottom of membrane 126 and base member 122, limits the "short circuiting" effects of such disruptions to a level where experiments can be conducted reliably and consistently.

In a preferred embodiment, membrane 126 is mounted in a rigid support or frame 150, facilitating transfer of the membrane to and from the test device and providing a degree of rigidity to membrane 126. Preferably, frame 150 comprises a ring or cup-shaped member as illustrated in FIGS. 3A and 3B. Such a membrane on a rigid support can be obtained, e.g., from Costar as Cat # 3419. However, it will be appreciated that other types and geometric configurations of frames may be provided to hold the membrane, including square, rectangular, triangular, oval, and the like.

Use of a cup-shaped frame is particularly advantageous in that such frames and membranes are commercially available as just described. In this way, known techniques may be employed to efficiently culture cells onto membrane 126. Once cultured, the membrane may be used to produce multiple wells within system 120 in a manner similar to system 100. In this way, the efficiency of the testing procedure is greatly increased. Further, the wells in system 120 are preferably arranged in a standard format, such as an 96 well array, so that system 120 may be used with standard tools similar to system 100.

As best shown in FIGS. 3A and 3B, frame 150 includes a lip 152. Base member 122 also includes a wall 154 having a groove or a guide 156. To position membrane 126 on base member 124, frame 150 is moved over face 140 until lip 152 is received into guide 156. Lip 152 slides within guide 154 until fully inserted as shown in FIG. 3A. In this way, wall 154 serves both to position frame 150 and membrane 126 at a known position relative to face 140 and to secure membrane 126 over face 140. Further, such a manner of insertion significantly reduces the chances for damaging the cells on membrane 126.

Once frame 150 is fully inserted, top member 124 is inserted into frame 150 until it rests on membrane 126. As best shown in FIG. 3B, top member includes a pair of alignment pins 157 (one being hidden from view) which protrude from lower face 133, and base member 122 includes a pair of corresponding holes 159 (one being hidden from view) in top face 140. Pins 157 and holes 159 serve to align top member 124 with base member 122 and to prevent rotation of the two members relative to each other to prevent damage to the cells on membrane 126.

Because frame 150 is at a known location relative to face 140, top member 124 is also at a known position relative to face 140. In this manner, a way is provided to reproducibly allow apertures 136 in top member to be aligned with wells 123 in base member each time the system is assembled. After assembly, screws (not shown) are screwed into holes 158 of top member 124 and into holes 160 of base member to secure membrane 126 between top member 124 and base member 122. However, it will be appreciated that other securing devices may be used, including clamps, latches, and the like.

One particular advantage of system 120 is that multiple base members may be provided, with each base member having wells which define a different volume. In this way, the flow rate of substances into the wells may be controlled simply by selecting a base member with the appropriately sized wells.

System 120 may be operated in a manner similar to system 100 to perform permeations tests. Once the experiment is finished, samples may be withdrawn from apertures 136. Apertures 136 are then washed with a solvent one or more times. Membrane 126 may then be removed or punctured to access wells 123 to allow the solution to be extracted. As previously described either manual or automated equipment may be employed to add and withdraw the various fluids.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A testing system, comprising:
   a base member having a plurality of wells;
   a top member having a plurality of apertures, at least some of which correspond to the wells in the base member; and
   a membrane sheet coupled to a frame, wherein the membrane sheet is adapted to receive a layer of cells and to be placed between the top member and the base member, wherein a substance within the apertures may permeate through the membrane and into the wells.

2. A system as in claim 1, further comprising a gasket which is adapted to be placed between the base member and the top member.

3. A system as in claim 1, further comprising a securing mechanism to secure the top member to the base member.

4. A system as in claim 1, wherein the membrane is constructed of a material selected from the group of materials consisting of polytetrafluroethylene, polyethylene, PET and polycarbonate.

5. A system as in claim 1, wherein the cells comprise mammalian based cells.

6. A system as in claim 1, wherein the frame comprises a geometrically-shaped member disposed around a periphery of the membrane.

7. A system as in claim 6, wherein the base member includes a guide to receive at least a portion of the frame to allow the membrane to be positioned on the base member at a known location.

8. A system as in claim 7, wherein the top member is received into the frame to assist in aligning the apertures with the wells.

9. A system as in claim 1, wherein the wells and apertures are arranged in a two dimensional array.

10. A system as in claim 1, further comprising a second base member having wells with a different volume than the wells of the first base member.

11. A method for performing assays, comprising:
    providing a base member having a plurality of wells, and a top member having a plurality of apertures;
    growing cells onto a membrane sheet that is coupled to a frame;
    grasping the frame and positioning the membrane sheet onto the base member;
    placing the top member over the membrane;
    securing the top member to the base member such that at least some of the wells are aligned with at least some of the apertures;
    introducing a substance into the aligned apertures and allowing the substance to permeate the membrane sheet; and
    evaluating a characteristic of the substance within the wells.

12. A method as in claim 11, wherein the characteristic comprises the concentration of the substance, and further comprising determining a permeation rate of the substance through the membrane sheet.

13. A method as in claim 11, further comprising filling the wells with a buffer solution prior to placement of the membrane sheet between the top member and the base member.

14. A method as in claim 11, further comprising maintaining the substance within a desired temperature range.

15. A method as in claim 11, further comprising horizontally orienting the membrane sheet during permeation.

16. A method as in claim 11, further comprising vertically orienting the membrane sheet during permeation.

17. A method as in claim 11, further comprising removing the membrane sheet from the base layer or puncturing the membrane sheet to evaluate the characteristic.

18. A method as in claim 11, wherein the membrane is coupled to a frame, and further comprising inserting at least a portion of the frame into a guide of the base member and inserting the top member into the frame until the top member rests on the membrane.

19. A testing system, comprising:

a base member having a first face and a plurality of wells, each well having a top end defining a well perimeter in the first face, and a bottom end;

a top member having second and third faces and an array of apertures spaced to correspond to the wells in the base member, wherein each aperture extends from the second face to the third face to define an aperture perimeter in the third face;

a membrane sheet adapted to receive a layer of cells and to be placed between the top member and the base member, wherein for each corresponding aperture and well, the aperture perimeter is greater than the well perimeter; and a frame coupled to the membrane sheet.

20. A system as in claim 19, further comprising a gasket disposed against the third face, and wherein the gasket has a plurality of openings which are aligned with the aperture perimeters.

21. A system as in claim 19, further comprising a securing mechanism to secure the top member to the base member.

22. A system as in claim 19, wherein the membrane sheet is constructed of a material selected from the group of materials consisting of polytetrafluroethylene, polyethylene, PET and polycarbonate.

23. A system as in claim 19, wherein the frame comprises a gemoetrically-shaped member disposed around a periphery of the membrane.

24. A system as in claim 19, wherein the base member includes a guide to receive at least a portion of the frame to allow the membrane to be positioned on the base member at a known location.

25. A system as in claim 24, wherein the top member is received into the frame to assist in aligning the apertures with the wells.

26. A system as in claim 19, wherein the wells and apertures are arranged in a two dimensional array.

27. An apparatus for testing permeability of a sheet of cells on one side of a membrane, comprising:

a base member having a first face and a plurality of wells, each well having a top end defining a well perimeter in the first face, and a bottom end;

a top member having second and third faces and an array of apertures spaced to correspond to the wells in the base member, wherein each aperture extends from the second face to the third face to define an aperture perimeter in the third face;

a clamping mechanism to secure the membrane between the top and base members, wherein for each corresponding aperture and well, the aperture perimeter is greater than the well perimeter; and a gasket disposed against the third face, and wherein the gasket has a plurality of openings which are aligned with the aperture perimeters.

28. An apparatus for testing permeability of a sheet of cells on one side of a membrane, comprising;

a base member having a plurality of wells, each well having a top end and a bottom end;

a top member having a plurality of apertures, each having a top opening and a bottom opening, said bottom openings each defining a beveled edge, wherein said apertures are spaced to correspond to the wells; and a clamping mechanism to secure said membrane between said top and base members.

29. A system as in claim 28, further comprising a frame coupled to the membrane.

30. A system as in claim 29, wherein the frame comprises a geometrically-shaped member disposed around a periphery of the membrane.

31. A testing system, comprising:

a base member having a first face and a plurality of wells, each well having a top end defining a well perimeter in the first face, and a bottom end;

a top member having second and third faces and an array of apertures spaced to correspond to the wells in the base member, wherein each aperture extends from the second face to the third face to define an aperture perimeter in the third face;

a membrane sheet adapted to receive a layer of cells and to be placed between the top member and the base member, wherein for each corresponding aperture and well, the aperture perimeter is greater than the well perimeter, and wherein the membrane sheet is constructed of a material selected from the group of materials consisting of polytetrafluroethylene, polyethylene, PET and polycarbonate.

32. An apparatus for testing permeability of a sheet of cells on one side of a membrane, comprising:

a base member having a first face and a plurality of wells, each well having a top end defining a well perimeter in the first face, and a bottom end;

a top member having second and third faces and an array of apertures spaced to correspond to the wells in the base member, wherein each aperture extends from the second face to the third face to define an aperture perimeter in the third face;

a membrane disposed between the base and the top member; and a clamping mechanism to secure the membrane between the top and base members, wherein for each corresponding aperture and well, the aperture perimeter is greater than the well perimeter.

33. An apparatus as in claim 32, wherein the membrane is coupled to a frame, and wherein the apertures of the top member have a beveled edge.

* * * * *